US00PP14527P29

(12) United States Plant Patent
Johnson, Jr.

(10) Patent No.: US PP14,527 P2
(45) Date of Patent: Feb. 10, 2004

(54) HYDRANGEA PLANT NAMED 'BIG DADDY'

(50) Latin Name: *Hydrangea macrophylla*
Varietal Denomination: Big Daddy

(76) Inventor: Ozzie W. Johnson, Jr., 4363 Bishop Lake Rd., Marietta, GA (US) 30062

( * ) Notice: Subject to any disclaimer, the term of this patent is extended or adjusted under 35 U.S.C. 154(b) by 0 days.

(21) Appl. No.: 10/313,131

(22) Filed: Dec. 6, 2002

(51) Int. Cl.[7] ..... A01H 5/00

(52) U.S. Cl. ..... Plt./250

(58) Field of Search ..... Plt./250

*Primary Examiner*—Bruce R. Campell
*Assistant Examiner*—June Hwu
(74) *Attorney, Agent, or Firm*—C. A. Whealy

(57) ABSTRACT

A distinct cultivar of Hydrangea plant named 'Big Daddy', characterized by its large and vigorous growth habit; upright and rounded plant habit; large glossy dark green-colored leaves; and large inflorescences with large pink-colored flowers.

1 Drawing Sheet

Botanical classification/cultivar designation: *Hydrangea macrophylla* cultivar Big Daddy.

BACKGROUND OF THE INVENTION

The present Invention relates to a new and distinct cultivar of Hydrangea plant, botanically known as *Hydrangea macrophylla*, and hereinafter referred to by the cultivar name Big Daddy.

The new Hydrangea originated from a chance cross-pollination of two unidentified selections of *Hydrangea macrophylla*, not patented. The cultivar Big Daddy was discovered and selected by the Inventor as a single plant within the progeny of the stated cross-pollination in a controlled environment in Marietta, Ga. in May, 1996.

Asexual reproduction of the new cultivar by vegetative cuttings taken in Atlanta, Ga., since September, 1999, has shown that the unique features of this new Hydrangea are stable and reproduced true to type in successive generations.

SUMMARY OF THE INVENTION

Plants of the cultivar Big Daddy have not been observed under all possible environmental conditions. The phenotype may vary somewhat with variations in environment such as temperature and light intensity without, however, any variance in genotype.

The following traits have been repeatedly observed and are determined to be the unique characteristics of 'Big Daddy'. These characteristics in combination distinguish 'Big Daddy' as a new and distinct cultivar:

1. Large and vigorous growth habit.
2. Upright and rounded plant habit.
3. Large glossy dark green-colored leaves.
4. Large inflorescences with large pink-colored flowers.

Plants of the new Hydrangea typically have larger leaves and inflorescences than other known selections of *Hydrangea macrophylla.*

Plants of the new Hydrangea can be compared to plants of the *Hydrangea macrophylla* cultivar Nikko Blue, not patented. In side-by-side comparisons conducted in Atlanta, Ga., plants of the new Hydrangea differed from plants of the cultivar Nikko Blue in the following characteristics:

1. Plants of the new Hydrangea had darker green-colored, glossier and larger leaves than plants of the cultivar Nikko Blue.
2. Plants of the new Hydrangea had stronger and thicker stems than plants of the cultivar Nikko Blue.
3. Plants of the new Hydrangea had larger inflorescences than plants of the cultivar Nikko Blue.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new Hydrangea.

The photograph at the top of the sheet is a close-up view of a typical flowering plant of 'Big Daddy'.

The photograph at the bottom of the sheet comprises a close-up view of typical inflorescence of a plant of 'Big Daddy'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and in the following description were grown in Atlanta, Ga. in two-gallon containers in an outdoor nursery and under conditions which closely approximate commercial production conditions. Plants were about two years old when the photographs and description were taken. The photographs and description were taken during the early summer.

Botanical classification: *Hydrangea macrophylla* cultivar Big Daddy.

Parentage:

*Male, or pollen, parent.*—Unidentified *Hydrangea macrophylla* selection, not patented.

*Female, or seed, parent*.—Unidentified *Hydrangea macrophylla* selection, not patented.

Propagation:

*Type cutting*.—By vegetative cuttings.

*Time to initiate roots*.—About 10 days at 75° F.

*Time to produce a rooted cutting or liner*.—About 60 days at 75° F.

*Root description*.—Fine.

*Rooting habit*.—Freely branching.

Plant description:

*Form/growth habit*.13 Upright and rounded plant habit; bushy perennial shrub. Tall and vigorous growth habit.

*Plant height, soil level to top of plant plane*.—About 58 cm.

*Plant diameter or area of spread*.—About 66 cm.

*Branching habit*.—When pinched, freely branching with about twelve lateral branches per plant.

*Lateral branches*.—Length: About 53 cm. Diameter: About 8 mm. Internode length: About 6.5 cm. Texture: New growth, smooth; mature, woody with lenticels. Lenticel quantity per linear 10 cm of stem: More than 50. Lenticel length: About 2 mm. Lenticel width: About 1 mm. Color: Young stems: Close to 144A. Mature stems: Closest to between 199A and 199B. Lenticels: Close to 166A to 166B.

*Foliage description*.—Leaves large, glossy, simple, opposite and durable. Length: About 15 cm. Width: About 10 cm. Shape: Ovate. Apex: Acute with cuspidate tendencies. Base: Obtuse. Margin: Serrulate. Texture, upper and lower surfaces: Smooth, glabrous. Venation pattern: Pinnate. Color: Young foliage, upper surface: Close to 147A. Young foliage, lower surface: Close to 147B. Mature foliage, upper surface: Close to 147A. Mature foliage, lower surface: Close to 147A to 147B. Venation, upper surface: 146C to 146D. Venation, lower surface: 144C to 144D. Petiole: Length: About 1.8 cm. Diameter: About 4 mm. Texture, upper and lower surfaces: Smooth, glabrous. Color, upper and lower surfaces: 146B to 146C.

Flower description:

*Flower type and habit*.—Single flowers arranged on terminal globular panicles with large showy sepals. Flowers persistent. Fragrance, not detected.

*Natural flowering season*.—Continuously flowering during the early summer in Atlanta, Ga.

*Flower longevity*.—Flowers last about four weeks on the plant.

*Quantity of flowers*.—Freely flowering; typically more than 300 flowers per panicle.

*Panicle length*.—About 15 cm.

*Panicle diameter*.—About 25 cm.

*Flower diameter*.—About 4 cm.

*Flower depth* (*height*).—About 6 mm.

*Flower buds*.—Length: About 3 mm. Diameter: About 2 mm. Shape: Globulose. Color: 145A.

*Petals*.—Arrangement: About four in a single whorl. Length: About 1 mm. Width: About 1 mm. Shape: Roughly ovate. Apex: Acute to rounded. Base: Attenuate. Margin: Entire. Texture, upper and lower surfaces: Smooth, glabrous. Color, upper and lower surfaces: 63C to 63D.

*Sepals*.—Arrangement: About four in a single whorl. Length: About 2 cm. Width: About 2 cm. Shape: Obovate. Apex: Rounded to slightly acute. Base: Attenuate. Margin: Entire. Texture, upper and lower surfaces: Smooth, glabrous. Color: When opening, upper surface: 145A. When opening, lower surface: 145A to 145B. Fully opened, upper surface: 63C; color becoming closer to 145A with development. Fully opened, lower surface: 63C to 63D; color becoming closer to 145A to 145B with development.

*Pedicels*.—Angle: About 45° from vertical. Strength: Moderately strong. Length: About 2.5 cm. Diameter: About 1.5 mm. Color: Close to 63D.

*Peduncles*.—Angle: Upright. Strength: Moderately strong. Length: About 4 cm. Diameter: About 4 mm. Color: 144A.

*Reproductive organs*.—Stamens: Quantity per flower: About four or five. Anther shape: Spherical. Anther length: About 0.5 mm. Anther color: 95D. Pollen amount: Scarce. Pollen color: 10D. Pistils: Pistil quantity per flower: One. Pistil length: About 1 mm. Stigma shape: Two to three-lobed. Stigma color: 63D. Style length: About 0.5 mm. Style color: 63D. Ovary color: 144B. Fruit/seed: Fruit and seed production has not been observed.

Disease/pest resistance: Under commercial production conditions, plants of the new Hydrangea have been observed to be somewhat resistant to Powdery Mildew. Plants have not been observed to be resistant to other pathogens or pests common to Hydrangea.

Weather tolerance: Plants of the new Hydrangea have been shown to be tolerant to temperatures ranging from 10 to more than 100° F. Flowers of plants have exhibited excellent tolerance to wind and rain.

It is claimed:

1. A new and distinct cultivar of Hydrangea plant named 'Big Daddy', as illustrated and described.

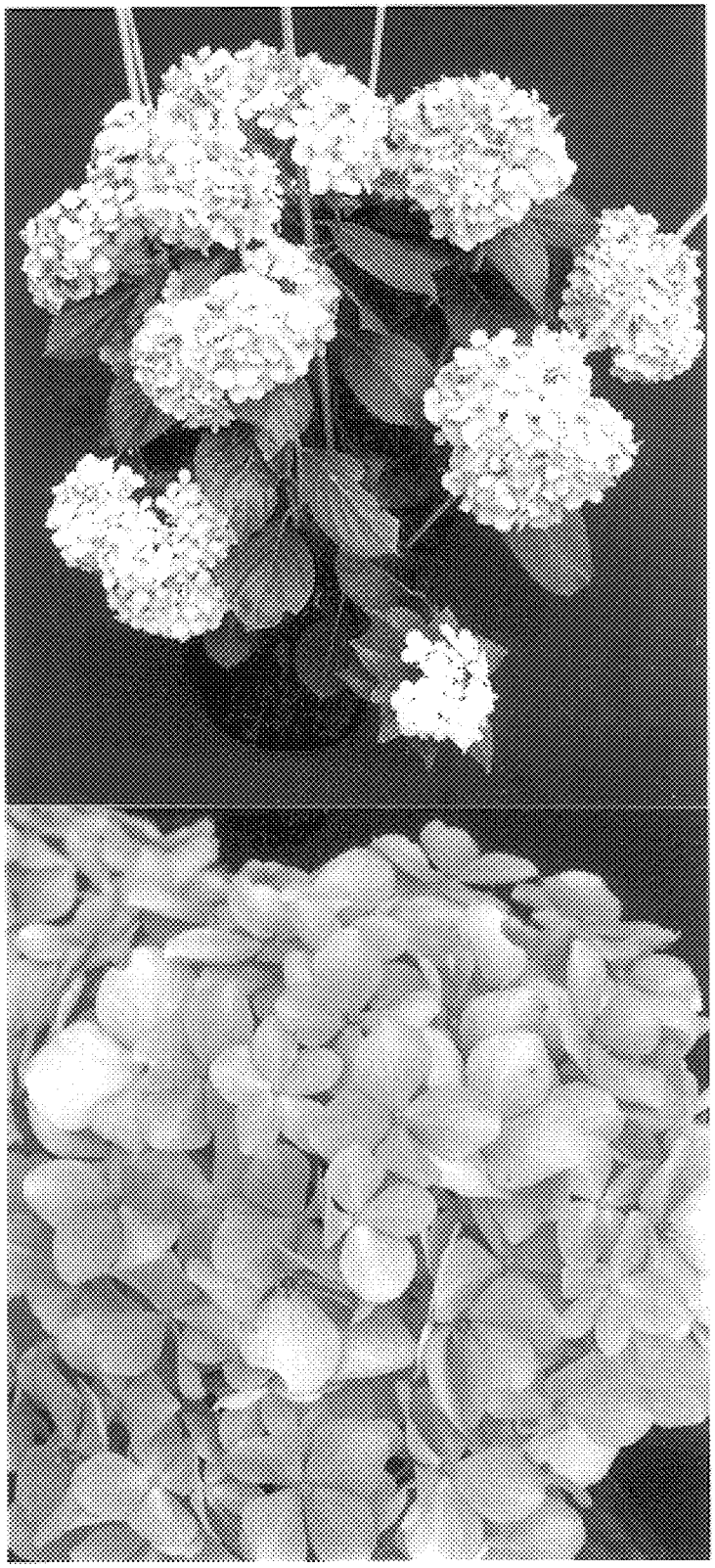

* * * * *